United States Patent
Tanaka et al.

(10) Patent No.: US 10,137,260 B2
(45) Date of Patent: Nov. 27, 2018

(54) NEBULIZER KIT AND NEBULIZER

(75) Inventors: Shinya Tanaka, Mishima-gun (JP);
Susumu Kutsuhara, Kyoto-shi (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 1124 days.

(21) Appl. No.: 13/534,668

(22) Filed: Jun. 27, 2012

(65) Prior Publication Data

US 2012/0266872 A1    Oct. 25, 2012

Related U.S. Application Data

(63) Continuation of application No. PCT/JP2011/052626, filed on Feb. 8, 2011.

(30) Foreign Application Priority Data

Mar. 16, 2010    (JP) .................................. 2010-059381

(51) Int. Cl.
*A61M 11/06*    (2006.01)

(52) U.S. Cl.
CPC ......... *A61M 11/06* (2013.01); *A61M 2209/06* (2013.01)

(58) Field of Classification Search
CPC ........ A61M 11/02; A61M 11/00; A61M 11/06
USPC ....................................... 128/200.14, 200.18
See application file for complete search history.

(56) References Cited

U.S. PATENT DOCUMENTS

| | | | |
|---|---|---|---|
| 5,865,171 A * | 2/1999 | Cinquin | A61M 11/005 128/200.14 |
| 6,543,701 B1 * | 4/2003 | Ho | B05B 17/0615 128/200.16 |
| 6,796,513 B2 * | 9/2004 | Fraccaroli | A61M 11/06 128/200.18 |
| 6,929,003 B2 * | 8/2005 | Blacker | A61M 11/06 128/200.24 |
| 7,581,718 B1 * | 9/2009 | Chang | A61M 11/06 128/200.18 |
| 7,712,466 B2 * | 5/2010 | Addington | A61B 5/08 128/200.19 |
| 7,721,729 B2 * | 5/2010 | Von Hollen | A61M 15/0085 128/200.14 |
| 8,025,054 B2 * | 9/2011 | Dunsmore | A61M 16/00 128/200.14 |

(Continued)

FOREIGN PATENT DOCUMENTS

| | | |
|---|---|---|
| EP | 1932559 A1 | 6/2008 |
| JP | A-60-199458 | 10/1985 |

(Continued)

OTHER PUBLICATIONS

International Preliminary Report on Patentability issued in International Application No. PCT/JP2011/052626 dated Jun. 11, 2012 (w/translation).

(Continued)

*Primary Examiner* — LaToya M Louis
(74) *Attorney, Agent, or Firm* — Oliff PLC

(57) ABSTRACT

The present nebulizer kit has a case body having a wall surface with a linear portion. The wall surface can serve as a barrier to change positively toward an aerosol discharge port a stream of aerosol flowing out from an external air introduction path in a direction away from the aerosol discharge port.

3 Claims, 9 Drawing Sheets

(56) References Cited

U.S. PATENT DOCUMENTS

| | | | |
|---|---|---|---|
| 8,596,263 B2* | 12/2013 | Piper | A61M 11/06 128/200.14 |
| 2006/0243274 A1* | 11/2006 | Lieberman | A61M 11/005 128/200.14 |
| 2007/0181133 A1* | 8/2007 | Boehm | A61M 11/02 128/207.18 |
| 2007/0227535 A1 | 10/2007 | Harrington et al. | |
| 2009/0272820 A1 | 11/2009 | Foley et al. | |
| 2010/0095958 A1* | 4/2010 | King | A61M 11/02 128/200.18 |

FOREIGN PATENT DOCUMENTS

| | | |
|---|---|---|
| JP | A-6-285168 | 10/1994 |
| JP | A-2000-51355 | 2/2000 |
| WO | WO 03/053500 A1 | 7/2003 |
| WO | WO 2008/111255 A1 | 9/2008 |
| WO | 2009113395 A1 | 9/2009 |

OTHER PUBLICATIONS

International Search Report issued in International Application No. PCT/JP2011/052626 dated Apr. 19, 2011.
May 11, 2014 Extended European Search Report issued in Patent Application No. 1175600.7.
Nov. 5, 2014 Extended European Search Report issued in Patent Application No. 11756003.7.

* cited by examiner

EXTERNAL AIR ⇨
AEROSOL ➡
COMPRESSED AIR ┈▷
(EXTERNAL AIR)

EXTERNAL AIR ⇨
AEROSOL ⬛▶
COMPRESSED AIR ┅▶
(EXTERNAL AIR)

EXTERNAL AIR ⇨
AEROSOL ➡
COMPRESSED AIR ⇢
(EXTERNAL AIR)

FIG.12

![Figure 12 diagram with labels: 132, 140, 101, 100D, 133, 130D, 103, 134d, 102, 111, XIII, M, 114b, 122, 120, 124, 116d, 114a, W, 110D, 114, 12]

EXTERNAL AIR ⇨
AEROSOL ➡
COMPRESSED AIR ⇢
(EXTERNAL AIR)

FIG.13

![Figure 13 diagram with labels: L1, L2, 103, 132, 110a, C1, 103, 110D, 134d, 102, 110b, M, 112, 124]

NEBULIZER KIT AND NEBULIZER

This is a continuation of application Ser. No. PCT/JP2011/052626 filed Feb. 8, 2011, the contents of which are incorporated herein by reference.

BACKGROUND OF THE INVENTION

Field of the Invention

The present invention relates generally to nebulizer kits and nebulizers.

Description of the Background Art

A nebulizer is a device for atomizing water, saline, drug preparations that are used to treat bronchial diseases and the like and other similar liquids to generate aerosol which is in turn taken by a user orally and/or nasally into his/her body. In recent years, an attempt has been made to aerosolize vaccines or the like for prevention of measles by the nebulizer and administer the aerosolized vaccines to the user orally and/or nasally.

Normally, a nebulizer has a main body device including a compressor generating compressed air and a nebulizer kit introducing the compressed air to generate aerosol. Such a nebulizer is disclosed in a prior art document, Japanese Patent Laying-open No. 06-285168. The nebulizer kit has a mouth piece, a mask and/or the like attached thereto as a component assisting the user for oral and/or nasal aspiration.

FIG. 14 shows a schematic configuration of a nebulizer kit in a horizontal cross section. The nebulizer kit has a spraying chamber S having a compressed air nozzle tip 301 (or an atomization unit) generally at its center to spray generated aerosol (indicated in the figure by arrows) toward the inner circumferential surface of a cylinder 300 of spraying chamber S uniformly.

However, while aerosol sprayed in a direction close to an aerosol discharge port 302 is dischargeable to aerosol discharge port 302, aerosol sprayed in a direction away from aerosol discharge port 302 (or a direction with aerosol discharge port 302 therebehind) is hardly guided to aerosol discharge port 302 rapidly.

SUMMARY OF THE INVENTION

The present invention has been made to overcome a portion of generated aerosol that is inefficiently discharged to an aerosol discharge port. Accordingly, the present invention contemplates a nebulizer kit and nebulizer allowing the nebulizer kit to spray aerosol more efficiently.

The present invention provides a nebulizer kit introducing compressed air to an atomization portion to generate aerosol, including: an external air introduction tube defining an external air introduction path introducing external air; the atomization portion provided at a center position of the external air introduction tube; and a case body surrounding the external air introduction tube and defining an aerosol carrier path communicating with an aerosol discharge port.

An aerosol stream changing portion is provided at a region of the aerosol carrier path located at a side opposite to the aerosol discharge port with the atomization portion posed therebetween to change positively toward the aerosol discharge port a stream of the aerosol flowing out in a direction away from the aerosol discharge port.

Preferably, the case body has a first wall surface at a side of the case body surrounding the external air introduction tube that is provided with the aerosol discharge port, as seen at the atomization portion, and a second wall surface at a side of the case body surrounding the external air introduction tube opposite to the side of the case body surrounding the external air introduction tube that is provided with the aerosol discharge port, as seen at the atomization portion, the second wall surface having a region, a distance from the region to the atomization portion being smaller than a distance from the first wall surface to the atomization portion, and the region configures the aerosol stream changing portion.

Preferably, the aerosol carrier path is provided with a suspended wall located inwardly of a wall surface located at a side opposite to a side provided with the aerosol discharge port, as seen at the atomization portion, and the suspended wall configures the aerosol stream changing portion.

Preferably, an extension is provided at a side of the external air introduction tube opposite to a side of the external air introduction tube provided with the aerosol discharge port, as seen at the atomization portion, and extends along the tube more than the side of the external air introduction tube provided with the aerosol discharge port, as seen at the atomization portion, and the extension configures the aerosol stream changing portion.

Preferably, as the aerosol stream changing portion, the atomization portion is positioned offset to a side opposite to a side provided with the aerosol discharge port, as seen at a center position of the case body.

The present invention provides a nebulizer including: a main body having a compressor outputting compressed air; a compressed air tube unit deriving the compressed air output from the compressor; and the above described nebulizer kit having one end of the compressed air tube unit coupled thereto to generate aerosol.

The present invention can thus provide a nebulizer kit and nebulizer that is capable of more efficiently spraying the aerosol generated in the nebulizer kit.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 12 is a longitudinal cross section of a nebulizer kit in a fourth embodiment, that corresponds to the view along the FIG. 3 arrow V-V.

FIG. 13 is a lateral cross section as seen along an arrow XIII-XIII of FIG. 12.

DESCRIPTION OF THE PREFERRED EMBODIMENTS

Figure 1:
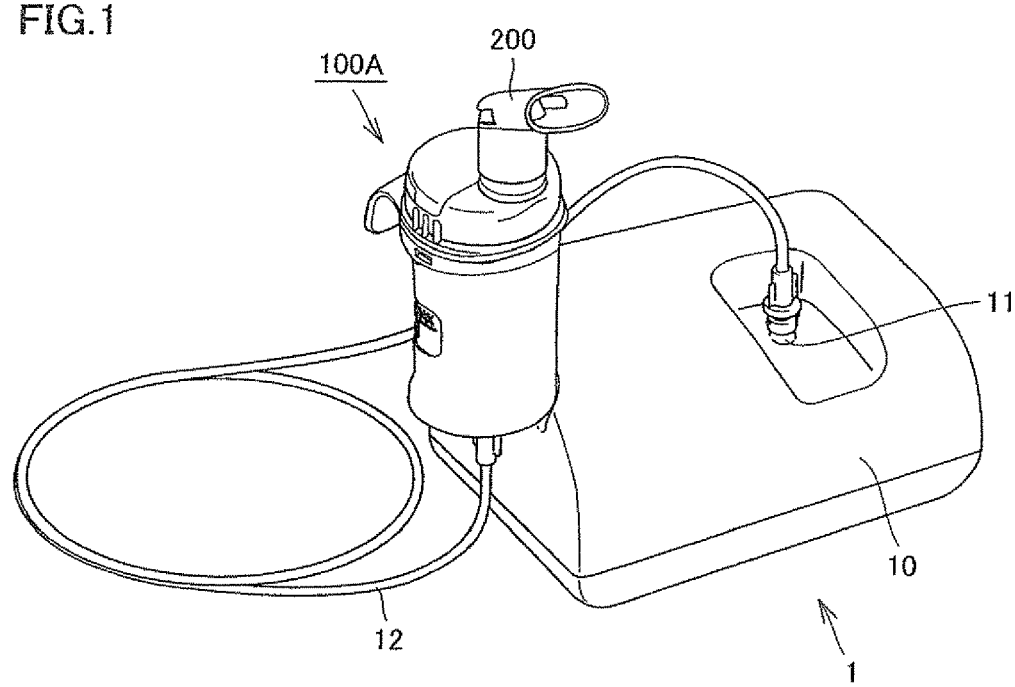
FIG. 1 is a general perspective view showing an appearance of a nebulizer in a first embodiment.

The present invention in each embodiment provides a nebulizer kit and nebulizer, as will more specifically be described hereinafter with reference to the drawings. It should be noted that in the following embodiments when numbers, amounts and the like are referred to, the present invention is not necessarily limited to the numbers, amounts and the like unless otherwise indicated. Furthermore, combining the following embodiments as appropriate is initially intended unless otherwise indicated. In the figures, identical reference characters denote identical or corresponding components and accordingly, the components may not be described repeatedly.

First Embodiment: Nebulizer 1 and Nebulizer Kit 100A

Hereinafter with reference to FIG. 1 to FIG. 6 a first embodiment provides a nebulizer 1 and a nebulizer kit 100A, as will be described hereinafter. Initially, with reference to FIG. 1 to FIG. 5, nebulizer 1 and nebulizer kit 100A are generally configured, as will be described hereinafter.

Figure 2:
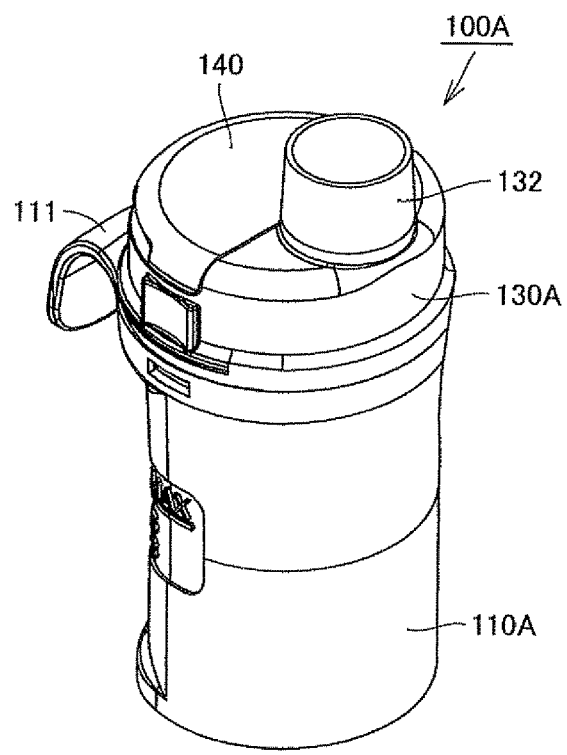
FIG. 2 is a first general perspective view showing an appearance of a nebulizer kit in the first embodiment.
Figure 3:
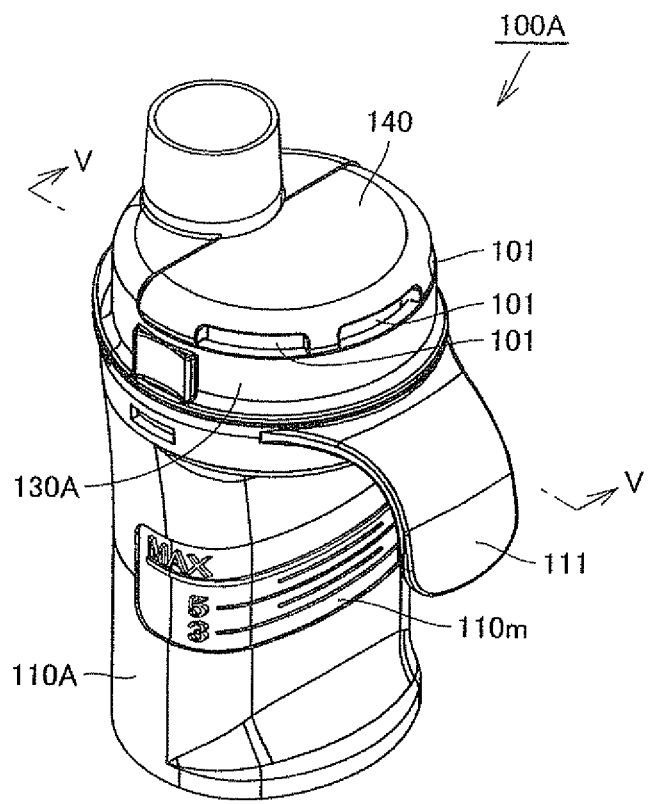
FIG. 3 is a second general perspective view showing an appearance of the nebulizer kit in the first embodiment.
Figure 4:
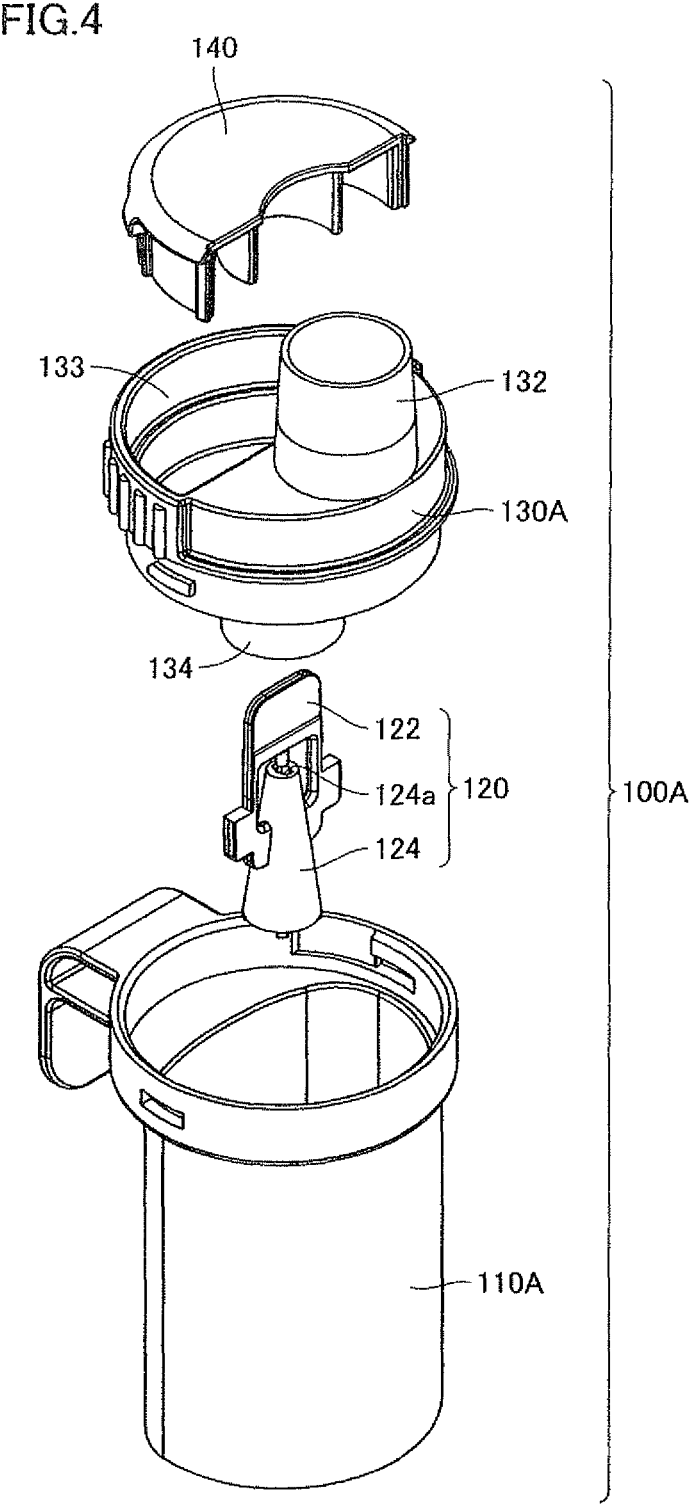
FIG. 4 is an exploded perspective view of the nebulizer kit in the first embodiment.
Figure 5:
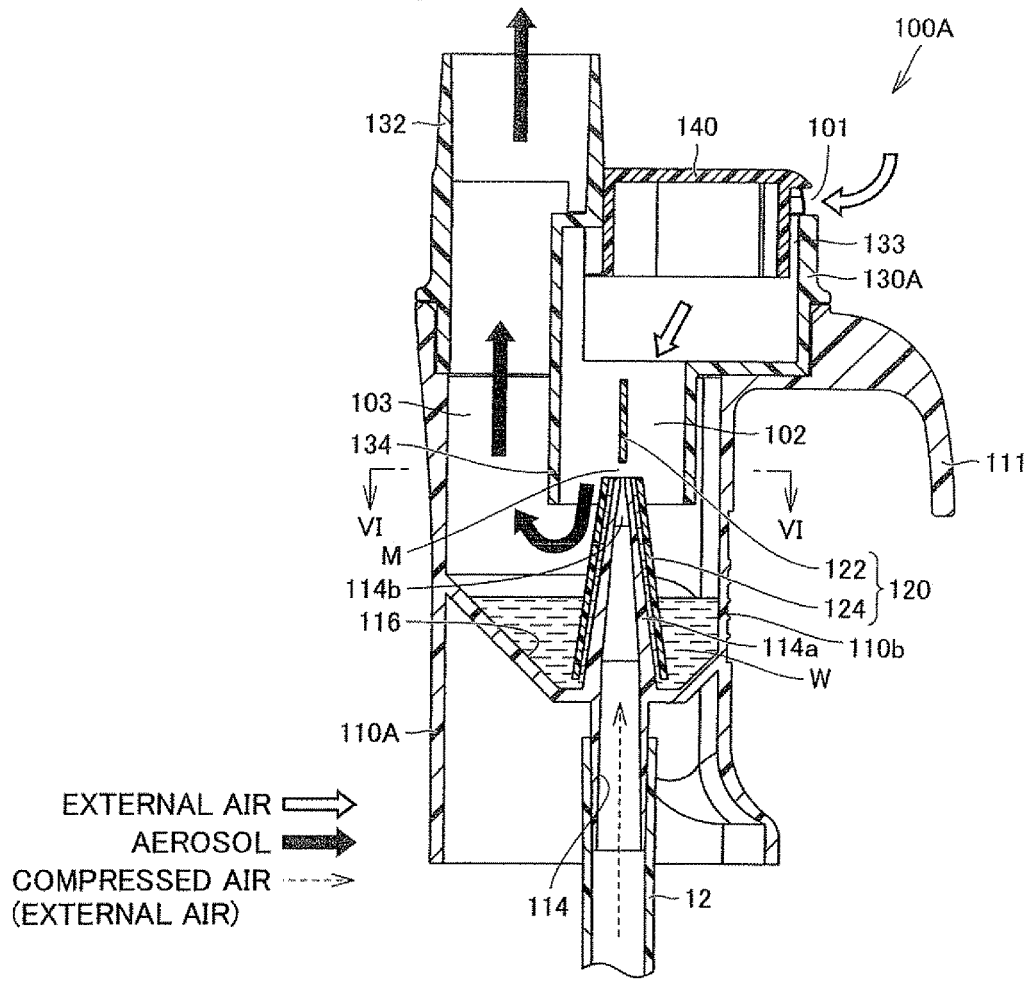
FIG. 5 is a longitudinal cross section as seen along an arrow V-V of FIG. 3.

FIG. 1 is a general perspective view showing an appearance of nebulizer 1. FIGS. 2 and 3 are first and second general perspective views showing nebulizer kit 100A in appearance. FIG. 4 is an exploded perspective view of nebulizer kit 100A. FIG. 5 is a longitudinal cross section as seen along an arrow V-V of FIG. 3.

With reference to FIG. 1, nebulizer 1 includes: a nebulizer main body 10 having a compressor outputting compressed air, electronic components and the like incorporated therein; a tube 12 serving as a flexible, compressed air tube unit having one end coupled to a compressed air blowing port 11 of nebulizer main body 10; nebulizer kit 100A having the other end of tube 12 coupled thereto; and a mouth piece 200 coupled with nebulizer kit 100A and serving as an aspiration assisting component assisting the user's oral and/or nasal aspiration. Mouth piece 200 is provided in a variety of forms, such as a mask.

With reference to FIG. 2 to FIG. 4, nebulizer kit 100A has a case body 110A, an atomization portion forming body 120, a flow path forming body 130A, and a cap body 140. Flow path forming body 130A has an upper surface having a cylindrical aerosol discharge port 132 having mouth piece 200 or a similar aspiration assisting component connected thereto.

With reference to FIG. 3, a grip 111 is provided on an external surface of case body 110A that is opposite to aerosol discharge port 132. Furthermore, a scale 110m is provided on an external surface of case body 110A under grip 111 for indicating an amount of a drug preparation accommodated in case body 110A. Furthermore, between cap body 140 and flow path forming body 130A, a plurality of pressure adjusting gaps 101 is provided.

With reference to FIG. 4, atomization portion forming body 120 has a conical, liquid aspiration tube forming body 124 having a top with an opening 124a, and a baffle 122 located exactly over opening 124a.

Case body 110A is a bottomed cylinder and has atomization portion forming body 120 accommodated therein. Flow path forming body 130A is attached to an upper portion of case body 110A so as to close an upper opening of case body 110A. Cap body 140 is attached to flow path forming body 130A so as to cover an opening 133 provided at an upper surface of flow path forming body 130A.

Case body 110A, atomization portion forming body 120, flow path forming body 130A, cap body 140 and tube 12 can be mutually disassembled and assembled, and are configured to be readily washed and disinfected after nebulizer 1 is used. Furthermore, mouth piece 200 or a similar aspiration assisting component is disposed after use in view of hygiene, i.e., is so-called disposable.

As shown in FIG. 5, flow path forming body 130A has a bottom surface provided with an external air introduction tube 134 coupled to an opening of aerosol discharge port 132. Case body 110A has a bottom surface provided with a vertically extending, compressed air introduction tube 114 for introducing the compressed air that is output from the compressor into case body 110A.

Compressed air introduction tube 114 has a lower end with tube 12 attached thereto. Furthermore, compressed air introduction tube 114 has an upper end 114a tapered toward a tip opening 114b.

A reservoir 116 is provided at a portion of case body 110A that surrounds compressed air introduction tube 114. Reservoir 116 temporarily reserves a liquid W such as water, saline, drug preparation used to treat bronchial diseases and the like, vaccine, and/or the like.

The compressed air introduction tube 114 upper end 114a is covered with the atomization portion forming body 120 liquid aspiration tube forming body 124 and the compressed air introduction tube 114 tip opening 114b is exposed at the liquid aspiration tube forming body 124 opening 124a and thus opposite to the atomization portion forming body 120 baffle 122.

Generating and Discharging Aerosol

Reference will now be made to FIG. 5 to describe how aerosol is generated and discharged. Note that in FIG. 5, an arrow indicated by a broken line indicates a stream of compressed air (or external air) output from nebulizer main body 10, a white arrow indicates a stream of external air introduced through pressure adjusting gap 101, and a black arrow indicates a stream of aerosol discharged.

A liquid aspiration tube is configured by a gap formed between liquid aspiration tube forming body 124 and the compressed air introduction tube 114 upper end 114a, and compressed air blown causes a negative pressure to act to cause liquid W reserved in reservoir 116 to reach a vicinity of an atomization portion described hereinafter.

An atomization portion M is formed between the compressed air introduction tube 114 upper end 114a and baffle 122. In atomization portion M, the compressed air introduced by nebulizer main body 10 into compressed air introduction tube 114 is blown through the compressed air introduction tube 114 upper end 114a toward baffle 122. In doing so, liquid W sucked up to a vicinity of atomization portion M by an action of a negative pressure generated in the atomization portion is blown by the action of the negative pressure described above to atomization portion M and blown to baffle 122 together with the compressed air.

This action causes liquid W to impinge on baffle 122 and thus become fine droplets and hence misty particles which are in turn provided to external air introduced into case body 110A (including external air introduced by nebulizer main body 10 and external air introduced through pressure adjusting gap 101, as will be described hereinafter, as the user exhales) to generate aerosol.

Above atomization portion forming body 120 are positioned flow path forming body 130A and cap body 140. Flow path forming body 130A diaphragms a space in case body 110A to form a flow path allowing an air stream to flow therethrough. Furthermore, cap body 140 is fitted in opening 133 provided at the upper surface of flow path forming body 130A, and a gap provided between flow path forming body 130A and cap body 140 forms pressure adjusting gap 101 allowing a space in the nebulizer kit to communicate externally.

More specifically, external air introduction tube 134 provided under flow path forming body 130A sections a space in case body 110A into a center portion and a peripheral portion, and a portion internal to external air introduction tube 134 defines an external air introduction path 102 and a region surrounded by an external side of external air introduction tube 134 and case body 110A defines aerosol carrier path 103.

External air introduction path 102 is a flow path for guiding the external air that is introduced through pressure adjusting gap 101 to atomization portion M, and aerosol carrier path 103 is a flow path for guiding the aerosol that is generated in atomization portion M to aerosol discharge port 132.

Case Body 110A

Figure 6:
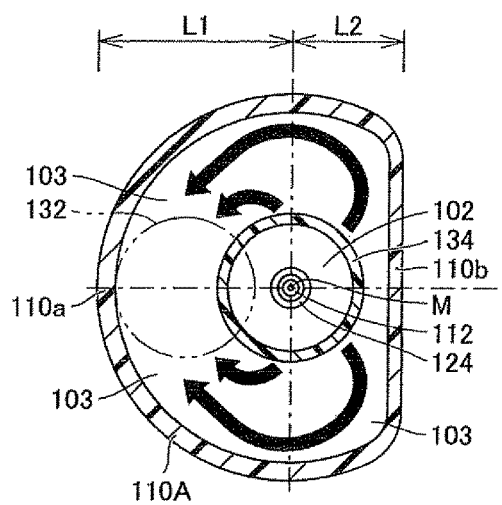
FIG. 6 is a lateral cross section as seen along an arrow VI-VI of FIG. 5.

Reference will now be made to FIG. 6 to describe a characteristic configuration of case body 110A in the present embodiment. FIG. 6 is a lateral cross section as seen along an arrow VI-VI of FIG. 5.

In the present embodiment, case body 110A has a wall surface 110a and a wall surface 110b. Wall surface 110a is located at a side of case body 110A surrounding external air introduction tube 134 that is provided with aerosol discharge port 132, as seen at atomization portion M, and wall surface 110b is located at a side of case body 110A surrounding external air introduction tube 134 opposite to the side of case body 110A surrounding external air introduction tube 134 that is provided with aerosol discharge port 132, as seen at atomization portion M. A distance (L2) from wall surface 110b to atomization portion M is smaller than a distance (L1) from wall surface 110a to atomization portion M.

More specifically, the wall surface of case body 110A at the side provided with aerosol discharge port 132, as seen at atomization portion M, is semicircular, and the wall surface of case body 110A opposite to the side provided with aerosol discharge port 132, as seen at atomization portion M, is provided with a linear portion (or a flat surface, when seen stereoscopically).

Case body 110A provided with wall surface 110b having a linear portion allows wall surface 110b to serve as a barrier so that a stream of aerosol that flows out from external air introduction path 102 in a direction away from aerosol discharge port 132 can be changed positively toward aerosol discharge port 132, as indicated in FIG. 6 by arrows. Note that in the present embodiment, the case body 110A wall surface 110b configures an aerosol stream changing portion.

Furthermore, an opening closer to aerosol discharge port 132, as seen at atomization portion M, is larger in area (or volume) than an opening opposite that closer to aerosol discharge port 132, as seen at atomization portion M. As a result, the aerosol is discharged against a resistance smaller at a side closer to aerosol discharge port 132 and larger at a side opposite to that closer to aerosol discharge port 132. The aerosol will thus be discharged more toward aerosol discharge port 132.

Function and Effect

The present embodiment thus provides nebulizer kit 100A that can direct aerosol to aerosol discharge port 132 and spray it more efficiently. As a result, nebulizer kit 100A with a compressor can spray aerosol in a larger amount per unit time than a conventional nebulizer kit with the same compressor. Furthermore, if nebulizer kit 100A may spray aerosol in the same amount per unit time as a conventional nebulizer kit, nebulizer kit 100A can be employed with a compressor having a reduced capacity and can thus contribute to a reduced cost for the main body.

Second Embodiment: Nebulizer Kit 100E

Figure 7:
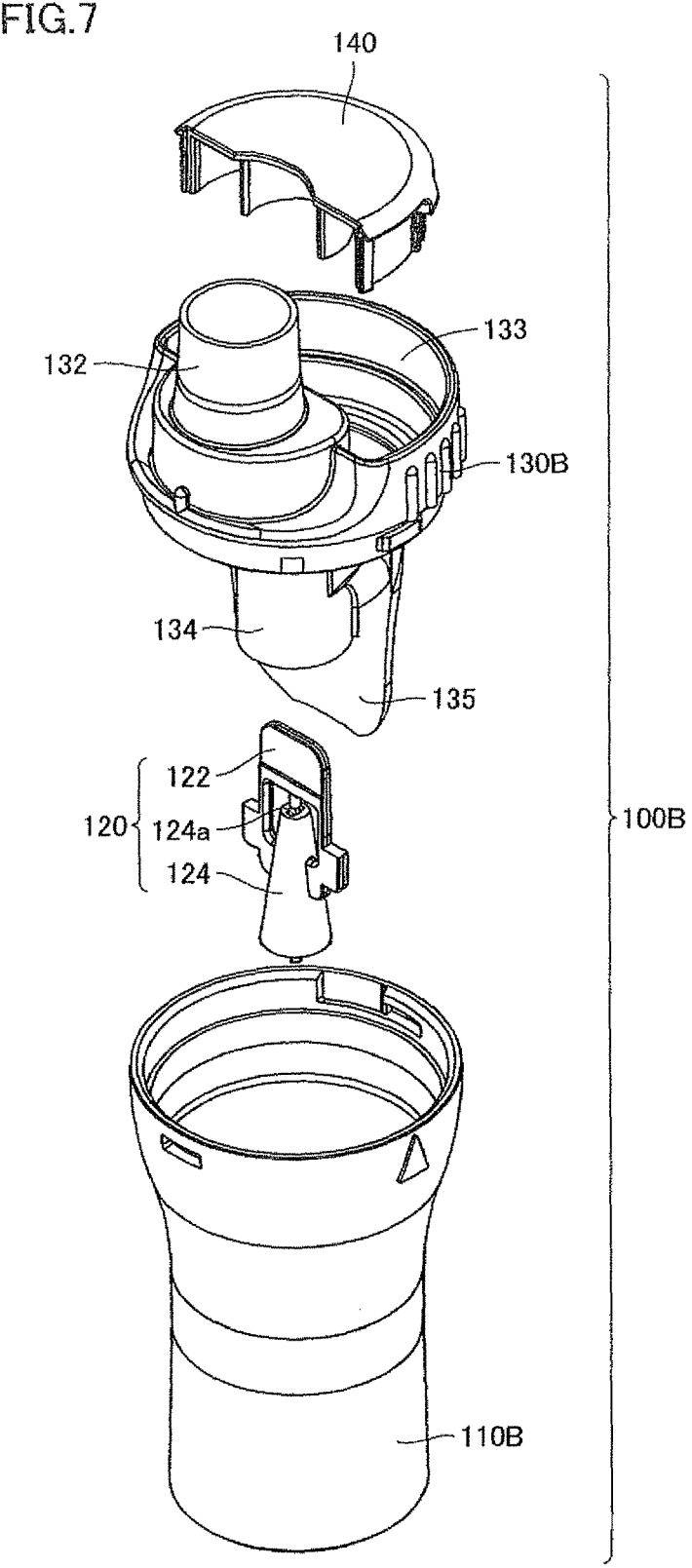
FIG. 7 is an exploded perspective view of an appearance of a nebulizer kit in a second embodiment.
Figure 8:
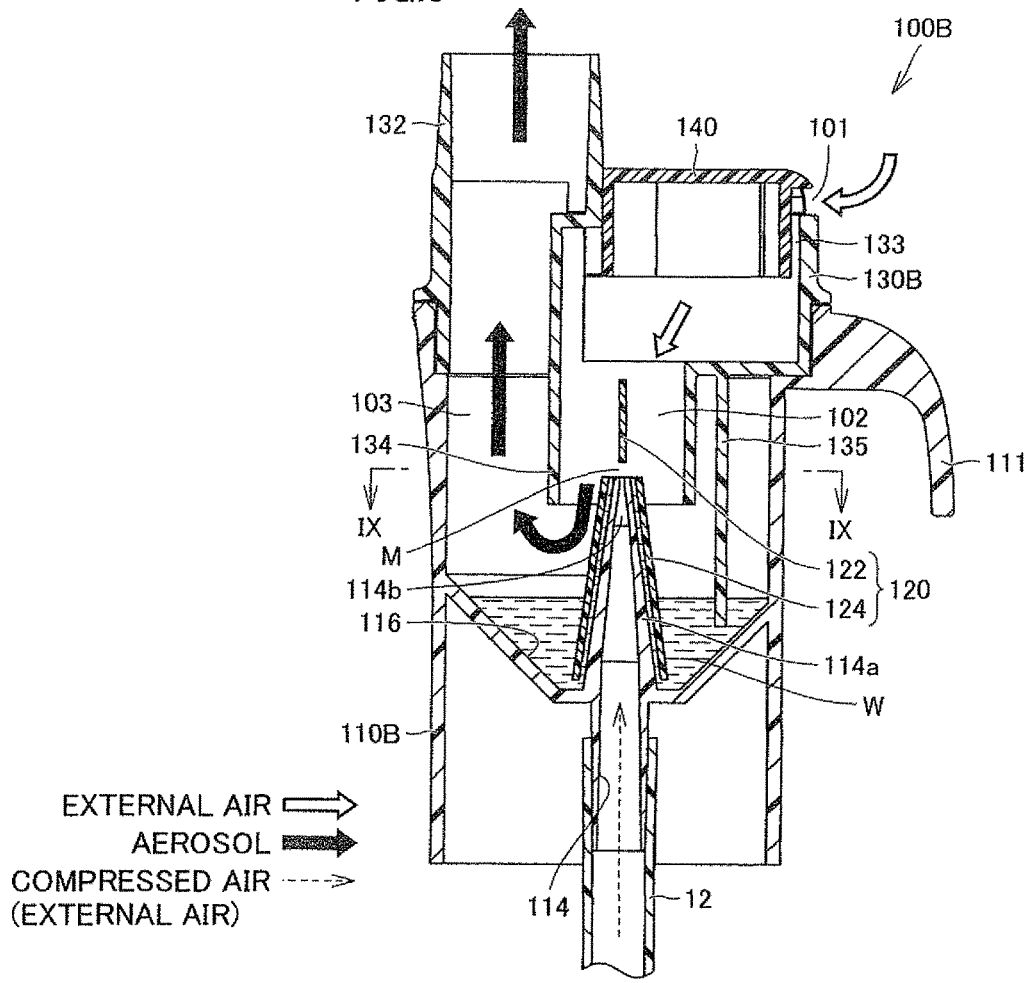
FIG. 8 is a longitudinal cross section of the nebulizer kit in the second embodiment, that corresponds to the view along the FIG. 3 arrow V-V.
Figure 9:
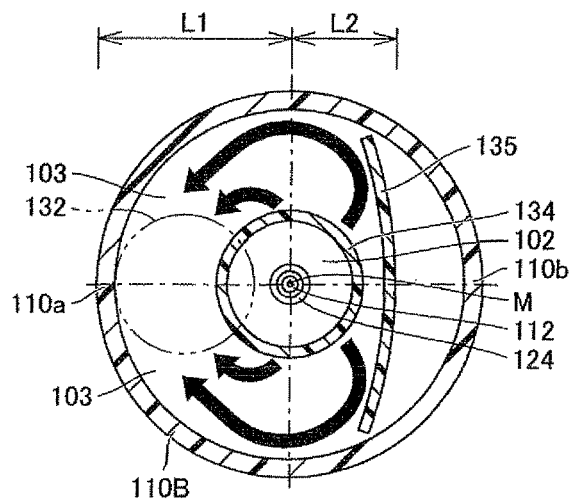
FIG. 9 is a lateral cross section as seen along an arrow IX-IX of FIG. 8.

With reference to FIG. 7 to FIG. 9, a second embodiment provides a nebulizer kit 100B as will be described hereinafter. Nebulizer 1 includes nebulizer main body 10, tube 12, and an aspiration assisting component, which are similar to those of the first embodiment, and accordingly, will not be described repeatedly. Furthermore, nebulizer kit 100B generates aerosol in a principle that is similar to that described in the first embodiment, and accordingly, will not be described repeatedly.

FIG. 7 is an exploded perspective view of an appearance of nebulizer kit 100B. FIG. 8 is a longitudinal cross section of nebulizer kit 100B that corresponds to the view along the FIG. 3 arrow V-V.

With reference to FIG. 7 and FIG. 8, the present embodiment provides nebulizer kit 100B different from nebulizer kit 100A in terms of a case body 110B and a flow path forming body 130B. The remainder in configuration is identical, and accordingly, how case body 110B and flow path forming body 130B are configured will be described hereinafter.

Case body 110B has a circular lateral cross section. The remainder in configuration is identical to case body 110A. Furthermore, flow path forming body 130B has aerosol carrier path 103 with a suspended wall 135 located inwardly of wall surface 110b located at a side of case body 110B surrounding external air introduction tube 134 opposite to a side of case body 110B surrounding external air introduction tube 134 that is provided with aerosol discharge port 132, as seen at atomization portion M. The remainder in configuration is identical to flow path forming body 130A.

Suspended wall 135 is formed to be gently curved to be recessed at a side closer to external air introduction tube 134, as shown in FIG. 7 and FIG. 9. Suspended wall 135 has a lower end reaching a vicinity of reservoir 116. Note that suspended wall 135 configures an aerosol stream changing portion. Furthermore, while the present embodiment provides case body 110B having a circular lateral cross section, it may alternatively adopt case body 110A as provided in the first embodiment.

Aerosol carrier path 103 thus having suspended wall 135 allows suspended wall 135 to serve as a barrier so that a stream of aerosol that flows out from external air introduction path 102 in a direction away from aerosol discharge port 132 can be changed positively toward aerosol discharge port 132, as indicated in FIG. 9 by arrows.

Furthermore, an opening closer to aerosol discharge port 132, as seen at atomization portion M, is larger in area (or volume) than an opening opposite that closer to aerosol discharge port 132, as seen at atomization portion M. As a result, the aerosol is discharged against a resistance smaller at a side closer to aerosol discharge port 132 and larger at a side opposite to that closer to aerosol discharge port 132. The aerosol will thus be discharged more toward aerosol discharge port 132.

Function and Effect

Thus, as well as the first embodiment, the present embodiment can also provide nebulizer kit 100B that can direct aerosol to aerosol discharge port 132 and spray it more efficiently. As a result, nebulizer kit 100B with a compressor can spray aerosol in a larger amount per unit time than a conventional nebulizer kit with the same compressor. Furthermore, if nebulizer kit 100B may spray aerosol in the same amount per unit time as a conventional nebulizer kit, nebulizer kit 100B can be employed with a compressor having a reduced capacity and can thus contribute to a reduced cost for the main body.

Third Embodiment: Case Body 110C

Figure 10:
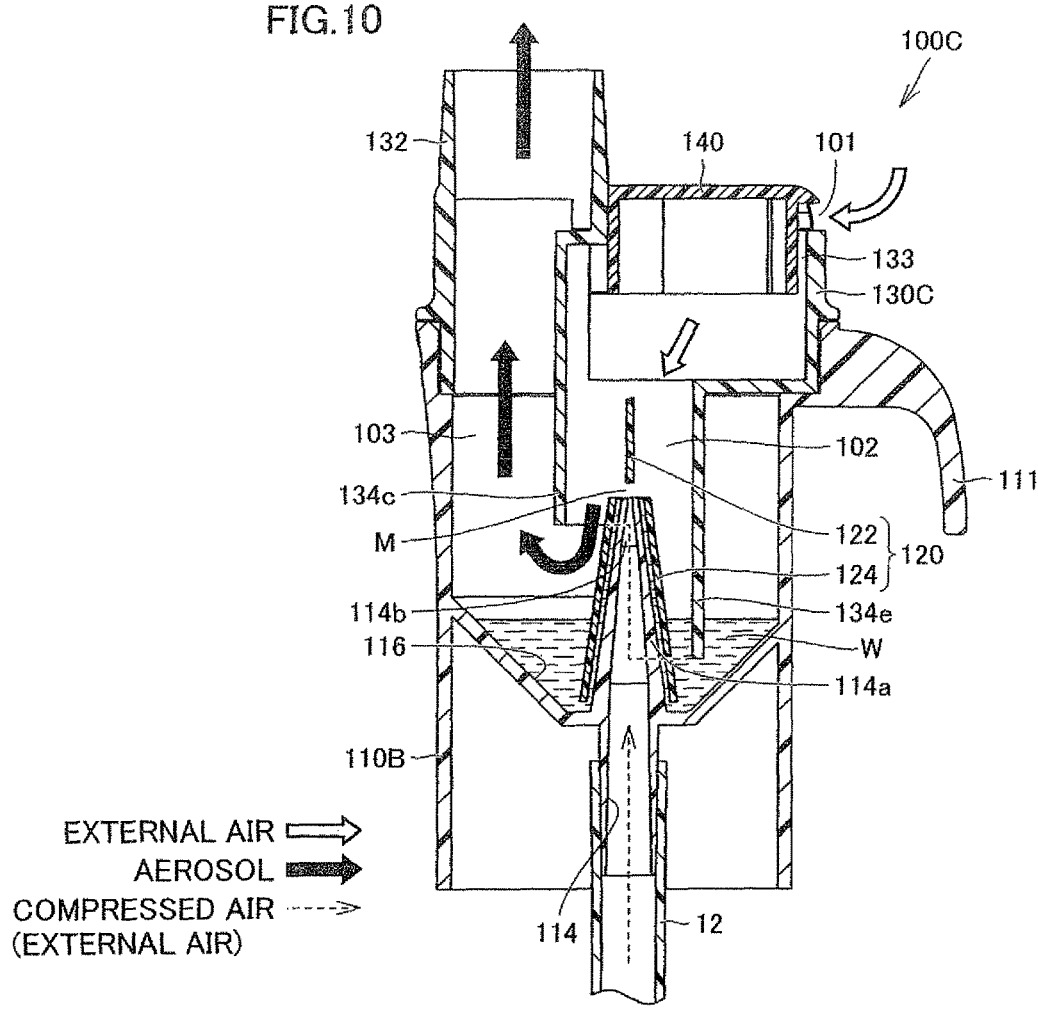
FIG. 10 is a cross section of a nebulizer kit in a third embodiment, that corresponds to the view along the FIG. 3 arrow V-V.
Figure 11:
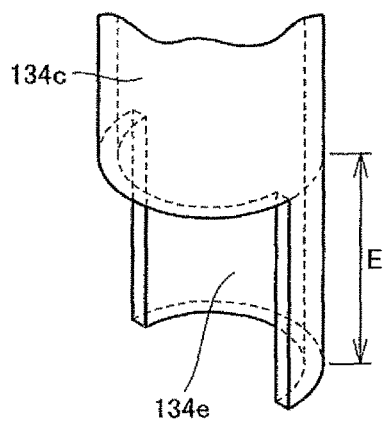
FIG. 11 is a partial, enlarged perspective view of an external air introduction tube of the nebulizer kit in the third embodiment.
Figure 14:
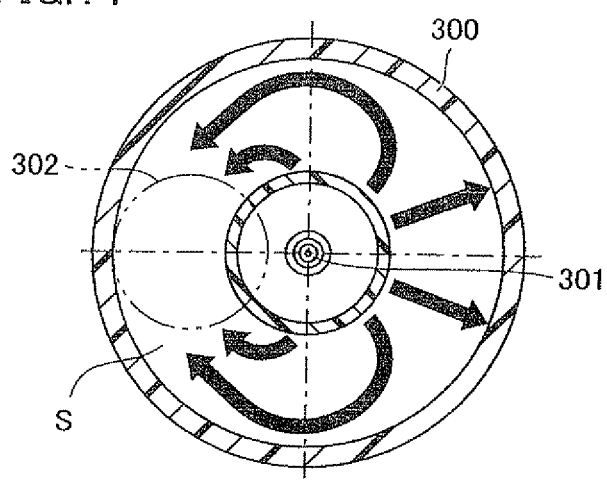
FIG. 14 is a lateral cross section of a nebulizer kit in a background art.

With reference to FIG. 10 to FIG. 11, a third embodiment provides a nebulizer kit 100C as will be described hereinafter. Nebulizer 1 includes nebulizer main body 10, tube 12, and an aspiration assisting component, which are similar to those of the first embodiment, and accordingly, will not be described repeatedly. Furthermore, nebulizer kit 100C generates aerosol in a principle that is similar to that described in the first embodiment, and accordingly, will not be described repeatedly.

FIG. 10 is a longitudinal cross section of nebulizer kit 100C that corresponds to the view along the FIG. 3 arrow V-V and FIG. 11 is a partial, enlarged perspective view of an external air introduction tube 134c of nebulizer kit 100C.

With reference to FIG. 10 and FIG. 11, the present embodiment provides nebulizer kit 100C different from nebulizer kit 100A in terms of case body 110B and a flow path forming body 130C. The remainder in configuration is identical, and accordingly, how case body 110B and flow path forming body 130C are configured will be described hereinafter.

Case body 110B is identical to that of the second embodiment, having a circular lateral cross section. Furthermore, flow path forming body 130C is provided with an extension 134e. Extension 134e is provided at a side of external air introduction tube 134c opposite to a side of external air introduction tube 134c provided with aerosol discharge port 132, as seen at atomization portion M, and extends along the tube more than the side of external air introduction tube 134c provided with aerosol discharge port 132, as seen at atomization portion M. Note that extension 134e configures an aerosol stream changing portion. The remainder in configuration is identical to flow path forming body 130A.

Extension 134e is semi-cylindrical and extends along the tube to be longer approximately by a length E than an end of external air introduction tube 134c located at aerosol discharge port 132, as shown in FIG. 11. Note that extension 134e configures the aerosol stream changing portion. Furthermore, while the present embodiment provides case body 110B having a circular lateral cross section, it may alternatively adopt case body 110A as provided in the first embodiment.

Aerosol carrier path 103 provided with extension 134e allows extension 134e to serve as a barrier so that a stream of aerosol that flows out from external air introduction path 102 in a direction away from aerosol discharge port 132 can be changed positively toward aerosol discharge port 132.

Furthermore, an opening closer to aerosol discharge port 132, as seen at atomization portion M, is larger in area (or volume) than an opening opposite that closer to aerosol discharge port 132, as seen at atomization portion M. As a result, the aerosol is discharged against a resistance smaller at a side closer to aerosol discharge port 132 and larger at a side opposite to that closer to aerosol discharge port 132. The aerosol will thus be discharged more toward aerosol discharge port 132.

Function and Effect

As well as the first embodiment, the present embodiment thus also provides nebulizer kit 100C that can direct aerosol to aerosol discharge port 132 and spray it more efficiently. As a result, nebulizer kit 100C with a compressor can spray aerosol in a larger amount per unit time than a conventional nebulizer kit with the same compressor. Furthermore, if nebulizer kit 100C may spray aerosol in the same amount per unit time as a conventional nebulizer kit, nebulizer kit 100C can be employed with a compressor having a reduced capacity and can thus contribute to a reduced cost for the main body.

Fourth Embodiment: Nebulizer Kit 100D

With reference to FIG. 12 to FIG. 13, a fourth embodiment provides a nebulizer kit 100D as will be described hereinafter. Nebulizer 1 includes nebulizer main body 10, tube 12, and an aspiration assisting component, which are similar to those of the first embodiment, and accordingly, will not be described repeatedly. Furthermore, nebulizer kit 100D generates aerosol in a principle that is similar to that described in the first embodiment, and accordingly, will not be described repeatedly.

FIG. 12 is a longitudinal cross section of nebulizer kit 100D that corresponds to the view along the FIG. 3 arrow V-V. FIG. 13 is a lateral cross section as seen along an arrow XIII-XIII of FIG. 12.

With reference to FIG. 12 and FIG. 13, the present embodiment provides nebulizer kit 100D different from nebulizer kit 100A of the first embodiment in terms of a case body 110D and a flow path forming body 130D. The remainder in configuration is identical, and accordingly, how case body 110D and flow path forming body 130D are configured will be described hereinafter.

Case body 110D is identical to that of the second embodiment, having a circular lateral cross section. Furthermore, compressed air introduction tube 114 does not have upper end 114a positioned at a center (C1) of case body 110D. Rather, compressed air introduction tube 114 has upper end 114a positioned offset to a side opposite to that provided with aerosol discharge port 132, as seen at atomization portion M. Furthermore, flow path forming body 130D also has an external air introduction tube 134d positioned offset to a side opposite to that provided with aerosol discharge port 132, as seen at atomization portion M. Note that atomization portion M is provided to be at the center position of external air introduction tube 134d. Furthermore, if case body 110D has a rectangular lateral cross section, then case body 110D has its center position (C1) generally at a position at which its diagonals cross.

Atomization portion M and external air introduction tube 134d offset to a side opposite to a side provided with aerosol discharge port 132, as seen at atomization portion M, configure an aerosol stream changing portion.

As atomization portion M and external air introduction tube 134d are offset to a side opposite to that provided with aerosol discharge port 132, as seen at atomization portion M, wall surface 110b provided at the side opposite to that provided with aerosol discharge port 132, as seen at atomization portion M, has a shorter distance to atomization portion M than wall surface 110a provided at the side provided with aerosol discharge port 132, as seen at atomization portion M, does.

Thus a stream of aerosol that flows out from external air introduction path 102 in a direction away from aerosol discharge port 132 can be changed positively toward aerosol discharge port 132, as indicated in FIG. 13 by arrows.

Furthermore, an opening closer to aerosol discharge port 132, as seen at atomization portion M, is larger in area (or volume) than an opening opposite that closer to aerosol discharge port 132, as seen at atomization portion M. As a result, the aerosol is discharged against a resistance smaller at a side closer to aerosol discharge port 132 and larger at a side opposite to that closer to aerosol discharge port 132. The aerosol will thus be discharged more toward aerosol discharge port 132.

Function and Effect

The present embodiment thus provides nebulizer kit 100D that can direct aerosol to aerosol discharge port 132 and spray it more efficiently. As a result, nebulizer kit 100D with a compressor can spray aerosol in a larger amount per unit time than a conventional nebulizer kit with the same compressor. Furthermore, if nebulizer kit 100D may spray aerosol in the same amount per unit time as a conventional nebulizer kit, nebulizer kit 100D can be employed with a compressor having a reduced capacity and can thus contribute to a reduced cost for the main body.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A nebulizer kit comprising:
an external air introduction tube defining an external air introduction path that introduces external air into the nebulizer kit;
an atomization portion that generates aerosol using compressed air from a compressed air tube unit, the atomization portion including a conically shaped liquid aspiration tube forming body that has an opening formed at both ends thereof, the atomization portion being provided at a center position within the external air introduction tube such that the external air introduction tube surrounds at least an upper portion of the atomization portion; and
a case body surrounding the external air introduction tube and defining an aerosol carrier path that communicates with an aerosol discharge port, the aerosol carrier path having at least a first region and a second region, the first region being located closer to the aerosol discharge port, and the second region being located opposite to the first region, wherein:
the case body includes an aerosol stream changing portion being provided in the second region of the aerosol carrier path, the atomization portion being located between the first region and the second region;
the aerosol changing portion is configured to redirect a stream of the aerosol flowing in a direction away from the aerosol discharge port to a direction toward the aerosol discharge port;
the case body is semicircular in shape and has a first curved wall surface that surrounds a portion of the external air introduction tube, the first wall surface is provided with the aerosol discharge port, and a second wall surface opposite to the first wall surface;
the second wall surface is a flat planar surface;
a distance from the second wall surface to the atomization portion along a horizontal plane passing through the atomization portion being smaller than a distance from the first wall surface to the atomization portion along the same horizontal plane;
the second wall surface is the aerosol stream changing portion;
the first region of the aerosol carrier path extends vertically through the case body;
the aerosol discharge port is directly disposed vertically above a reservoir that surrounds the external air introduction tube; and
the compressed air tube unit being off center from a vertical axis of the case body.

2. The nebulizer kit according to claim 1, wherein the atomization portion is positioned closer to the second region of the aerosol carrier path than to the first region of the aerosol carrier path.

3. A nebulizer comprising:
a main body having a compressor outputting compressed air; a compressed air tube unit deriving the compressed air output from the compressor; and
a nebulizer kit having one end of the compressed air tube unit coupled thereto, the nebulizer kit including:
an external air introduction tube defining an external air introduction path that introduces external air into the nebulizer kit;
an atomization portion that generates aerosol using compressed air from the compressed air tube unit, the atomization portion including a conically shaped liquid aspiration tube forming body that has an opening at both ends thereof, the atomization portion being provided at a center position within the external air introduction tube such that the external air introduction tube surrounds at least an upper portion of the atomization portion; and
a case body surrounding the external air introduction tube and defining an aerosol carrier path that communicates with an aerosol discharge port, the aerosol carrier path having at least a first region and a second region, the first region being located closer to the aerosol discharge port and the second region being located opposite to the first region, wherein:
the case body includes an aerosol stream changing portion being provided at the second region of the aerosol carrier path, the atomization portion being located between the first region and the second region;
the aerosol changing portion is configured to redirect a stream of the aerosol flowing in a direction away from the aerosol discharge port to a direction toward the aerosol discharge port;
the case body is semicircular in shape and has a first curved wall surface that surrounds a portion of the external air introduction tube, the first wall surface is provided with the aerosol discharge port, and a second wall surface opposite to the first wall surface;
the second wall surface is a flat planar surface;
a distance from the second wall surface to the atomization portion along a horizontal plane passing through the atomization portion being smaller than a distance from the first wall surface to the atomization portion along the same horizontal plane;
the second wall surface is the aerosol stream changing portion;
the first region of the aerosol carrier path extends vertically through the case body;

the aerosol discharge port is directly disposed vertically above a reservoir that surrounds the external air introduction tube; and the compressed air tube unit being off center from a vertical axis of the case body.

* * * * *